United States Patent [19]

Yerace et al.

[11] Patent Number: 4,854,162
[45] Date of Patent: Aug. 8, 1989

[54] METHOD OF LOCATING FRICTION GENERATING DEFECTS IN A MULTIPLE BEARING ASSEMBLY

[75] Inventors: Daniel Yerace, Belleville; Alexander J. Zinkosky, Dearborn, both of Mich.

[73] Assignee: Ford Motor Company, Dearborn, Mich.

[21] Appl. No.: 212,360

[22] Filed: Jun. 27, 1988

[51] Int. Cl.$^4$ .................. G01M 15/00; G01N 25/72
[52] U.S. Cl. .................................. 73/119 R; 374/4; 73/120
[58] Field of Search ............ 73/9, 116, 118.1, 119 R, 73/120; 374/4, 5, 7, 120, 121, 124, 129, 133, 137, 144; 250/330, 340, 342, 352, 359.1, 360.1, 491.1; 29/407

[56] References Cited
U.S. PATENT DOCUMENTS

| 2,745,969 | 5/1956 | Keller | 250/360.1 |
| 3,592,053 | 7/1971 | Lucia | 73/66 |
| 3,596,519 | 8/1971 | Blonder et al. | 374/4 |
| 3,718,757 | 2/1973 | Gulitz et al. | 374/124 |
| 3,886,912 | 6/1975 | Haglund | 123/200 |
| 3,921,435 | 11/1975 | Howard | 374/5 |
| 4,109,508 | 8/1978 | Fukuyama | 374/124 |
| 4,343,182 | 10/1982 | Pompei | 374/31 |
| 4,730,484 | 3/1988 | Olschefski | 73/119 R |
| 4,733,175 | 3/1988 | Levinson | 374/137 |

FOREIGN PATENT DOCUMENTS

| 1916800 | 4/1980 | Fed. Rep. of Germany | 73/119 R |
| 0051632 | 5/1981 | Japan | 374/124 |

OTHER PUBLICATIONS

NASA Tech Brief 69-10113, Jun. 1969.

Primary Examiner—Stewart J. Levy
Assistant Examiner—Robert R. Raevis
Attorney, Agent, or Firm—Joseph W. Malleck; Roger L. May

[57] ABSTRACT

A method of determining the location and type of dimensional defects, particularly friction generating defects, which comprises: (a) initiating simulated operation at ambient conditions of an assembly having certain sliding or rolling contact surfaces; (b) sensing any change in the temperature of such assembly surrounding each certain sliding or rolling contact surfaces (i) with a resolution of 0.02–1.0 C° (preferably 0.1–0.7 C°) and (ii) during a time span of 2–10 seconds measured from such initiation to provide separated voltage signals for each location; (c) converting the signals to a digitized thermal map; and (d) comparing the sensed digitized thermal map with a reference digitized thermal map for such an assembly without defects operated during the same time span and adjusted to compensate for any differing thermal conditions. Any deviations detected by such comparison representing defects.

14 Claims, 6 Drawing Sheets

```
┌─────────────────────────────────┐
│ Initiating Simulated Operation Of An │
│ Assembly Having Sliding Or Rolling │
│ Contact Surfaces                │
└─────────────────────────────────┘
                 │
┌─────────────────────────────────┐
│ Sensing Change In Temperature Of │
│ Such Assembly (i) Within A      │
│ Resolution Of .02 – 1.0° C And  │
│ (ii) During A Time Span Of 2 – 10 │
│ Seconds, Measured From Such     │
│ Initiation, To Provide a Voltage Signal │
└─────────────────────────────────┘
                 │
┌─────────────────────────────────┐
│ Digitizing Such Signal For Each │
│ Region of Assembly Surrounding  │
│ Such Sliding Or Rolling Contact │
│ Surfaces                        │
└─────────────────────────────────┘
                 │
┌─────────────────────────────────┐
│ Comparing The Sensed Digitized  │
│ Signal With A Reference Digitized │
│ Signal For Such An Assembly     │
│ Without Defects Operated During │
│ The Same Time Span And Adjusted │
│ To Compensate For Any           │
│ Differing Ambient Thermal       │
│ Conditions                      │
└─────────────────────────────────┘
```

METHOD OF LOCATING FRICTION GENERATING DEFECTS IN A MULTIPLE BEARING ASSEMBLY

BACKGROUND OF THE INVENTION

1. Technical Field

This invention relates to the art of sensing operational defects in piston and bearing assemblies and, more particularly, to sensing such defects at sliding and rolling contact areas of an engine.

2. Discussion of the Prior Art

It is conventional in the automotive industry to test a newly assembled engine by a simple screening process to identify engine assemblies that bind. A torque transducer is placed between an engine assembly output member and a drive motor; the motor essentially drives the mechanical elements of the engine assembly in a nonfiring condition. This is a cummulative sensing technique because it is possible that some parts may be too loose and some too tight; the total torque may mask the problem of the overly tight parts which may be close to binding. This technique does not locate the source of friction causing defects, it merely renders a consensus that there may be a problem somewhere in the engine assembly without identifying the location. Additionally, such torque transducer tests may permit burrs to gouge out an annular groove on the first turn of the test, permitting the torque to go back down to normal without revealing a permanent defect. If any defect is discovered by the torque transducer test, the engine must be withdrawn from the assembly line, disassembled, and explored as to location of possible problems. This is time-consuming, not always accurate. If the friction causing defect has become permanent as a result of scratching or binding and has been discovered, this will eventually require rework or scraping of the sliding or rolling bearing surfaces. If the friction causing defect has not been discovered because permanent grooving has taken place, the engine in regular use may, depending on the location of the defect, experience knocking, loss of oil pressure, seizure of crankshaft, or premature engine failure. To fix such defect in the field may cost 40 times what it would cost to fix the defect at the assembly line.

Similarly, dynamometer devices which sense an accumulation of delicate engine parameters while the engine is running hot are not useful to screen out friction causing defects because the sensing will be too late after damage has become permanent (see U.S. Pat. No. 3,592,053).

It would be desirable if dimensional or friction generating defects in newly assembled engines could be sensed by a technique that locates the defect in an extremely short time period, before the defect can damage the sliding or rolling surfaces and particularly before a friction binding part can penetrate the assembly oil film at such contact areas. It would further be desirable if radiation from such dimensional defects could be sensed sufficiently quickly and accurately to determine location and type of such defects before such damage can occur.

Heat sensors, such as those permanently incorporated, in a rotary engine (see U.S. Pat. No. 3,886,912), or valve body (see U.S. Pat. No. 3,921,435) to sense binding, are inappropriate for detection use in multiple bearing or piston assemblies such as a complex internal combustion engine; a large number of sensors, such as 15 or more, would have to be incorporated, increasing the cost and complexity.

Infrared radiation cameras have been used to monitor the heat pattern, on a gross or macroscale, of large storage tanks or containers, such heat pattern having been in existence for some time at a desirably constant level. A change in the heat pattern would signal the possibility of a lining breakthrough (see U.S. Pat. Nos. 4,343,182 and 3,596,519). Unfortunately, the use of radiation cameras in this limited manner is not adaptable to engine analysis since there is no preexisting heat pattern but only a small amount of heat that may be generated by the initial, but very limited, time period for motoring the engine assembly and before damage can occur to the sliding or rolling surfaces and particularly before damage can occur as a result of penetrating the assembly oil film present throughout the engine. Such time period is less than 15 seconds.

SUMMARY OF THE INVENTION

This invention has discovered: (a) that heat generation after only about two seconds of engine motoring is transmittable and can be detected by infrared thermography; and (b) that friction causing defects usually do not cause damage or penetrate the assembly oil film at a rolling or sliding contact surface in a time span of less than 10 seconds.

Based on these discoveries, the invention is a method of determining the location and type of dimensional defects in an assembly having sliding or rolling contact surfaces during simulated operation of the assembly and before damage results to such assembly. The method comprises: (a) initiating simulated operation of such assembly; (b) sensing any change in the temperature of the assembly surrounding the location of certain sliding or rolling contact surfaces (i) with a resolution power of as low as 0.02 C° but more practically in the range of 0.1–0.7 C° and (ii) during a time span of 2–10 seconds measured from such initiation to provide separated voltage signals for each location; (c) digitizing such signals; and (d) comparing the sensed digitized signals with reference digitized signals for such an assembly without defects operated during the same time span and adjusted to compensate for any differing thermal conditions, any deviations detected by such comparison representing defects. Preferably, the simulated operation is motoring of the cylinder block and crankcase subassembly. Motoring is used herein to mean driving an input or output member of an engine assembly or subassembly, at ambient temperature conditions without firing of the pistons, by use of an independent electric motor that turns such member at a speed typically about 750 rpm to generate perceptable temperature signals within a time span of less than 15 seconds. It is desirable to keep the speed as low as possible as long as data can be sensed in the desired time span.

Temperature sensing is preferably carried out by the use of infrared thermography which may use one of the following types of equipment: thermal camera, radiometer, and thermal line scanner. Temperature resolution is used herein to mean the smallest threshold unit of perception of a change in temperature detected by a thermal sensing unit.

Advantageously, one to three cameras may be deployed to scan a complex assembly with some of such cameras being eliminated by the use of mirrors. To eliminate interference from background lighting, the assembly may be placed in a black box.

SUMMARY OF THE DRAWINGS

FIG. 5 is a computer generated thermal map produced in accordance with this invention and depicting a defect in #4 cylinder bore.

DETAILED DESCRIPTION AND BEST MODE

Figure 1:
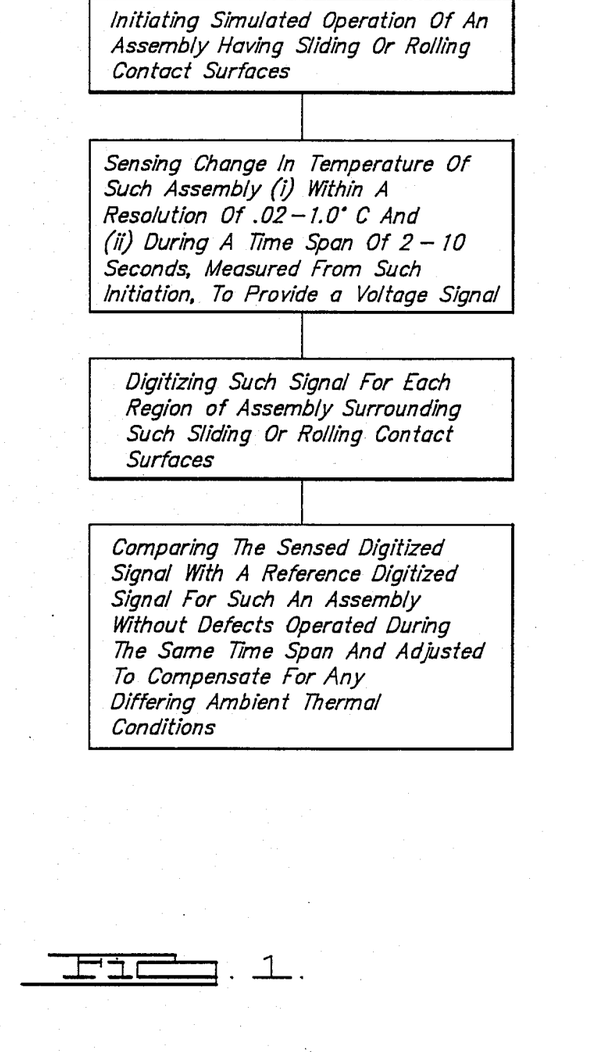
FIG. 1 is a basic flow diagram of the method steps of this invention.

As shown in FIG. 1, the method of this invention comprises: (a) initiating simulated operation of an assembly having certain sliding or rolling contact surfaces; (b) sensing change in the temperature of such assembly (i) within a resolution of 0.1–0.7 C° and (ii) during a time span of 2–10 seconds measured from such initiation to provide a voltage signal; (c) digitizing such signal for each region of the assembly surrounding such sliding or rolling contact surfaces; and (d) comparing the sensed digitized signal with a reference digitized signal for such an assembly without defects operated during the same time span and adjusted to compensate for any differing ambient thermal conditions.

Figure 1A:
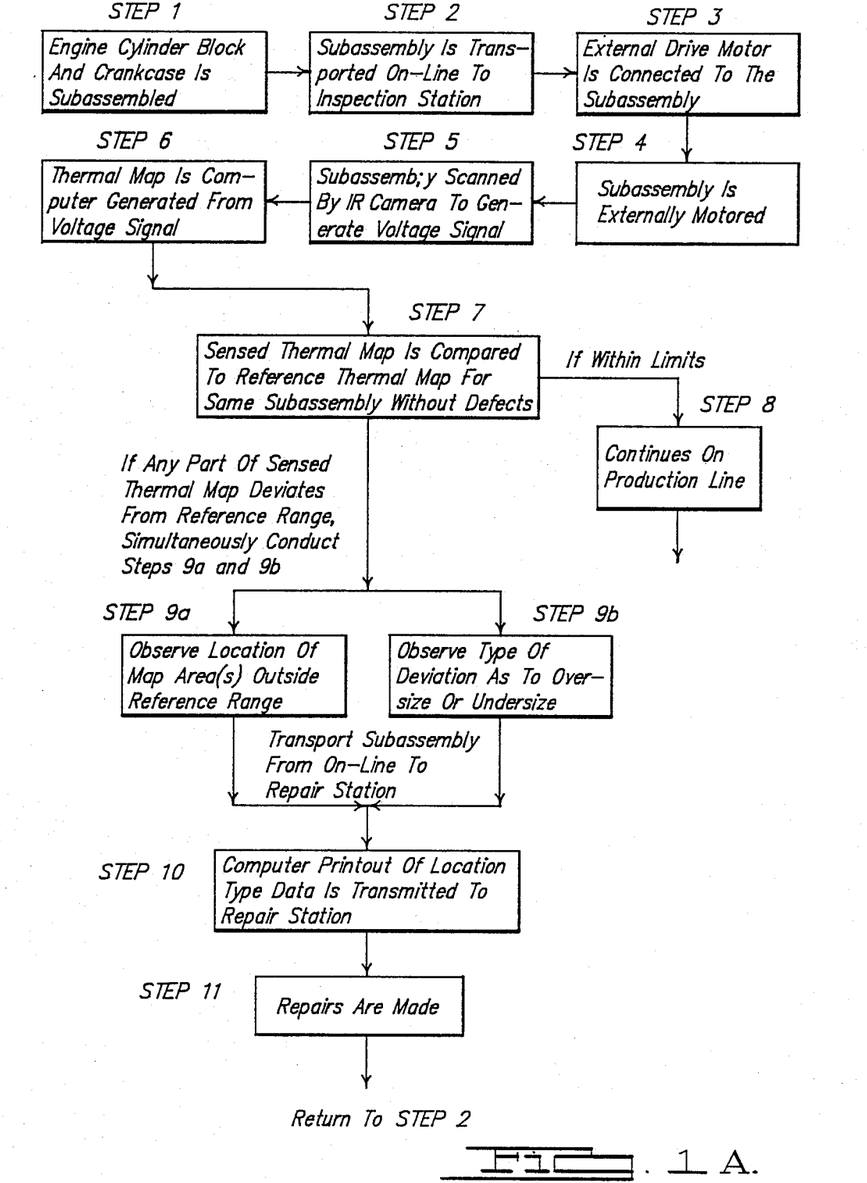
FIG. 1A is an amplified flow diagram of the preferred process.
Figure 2:
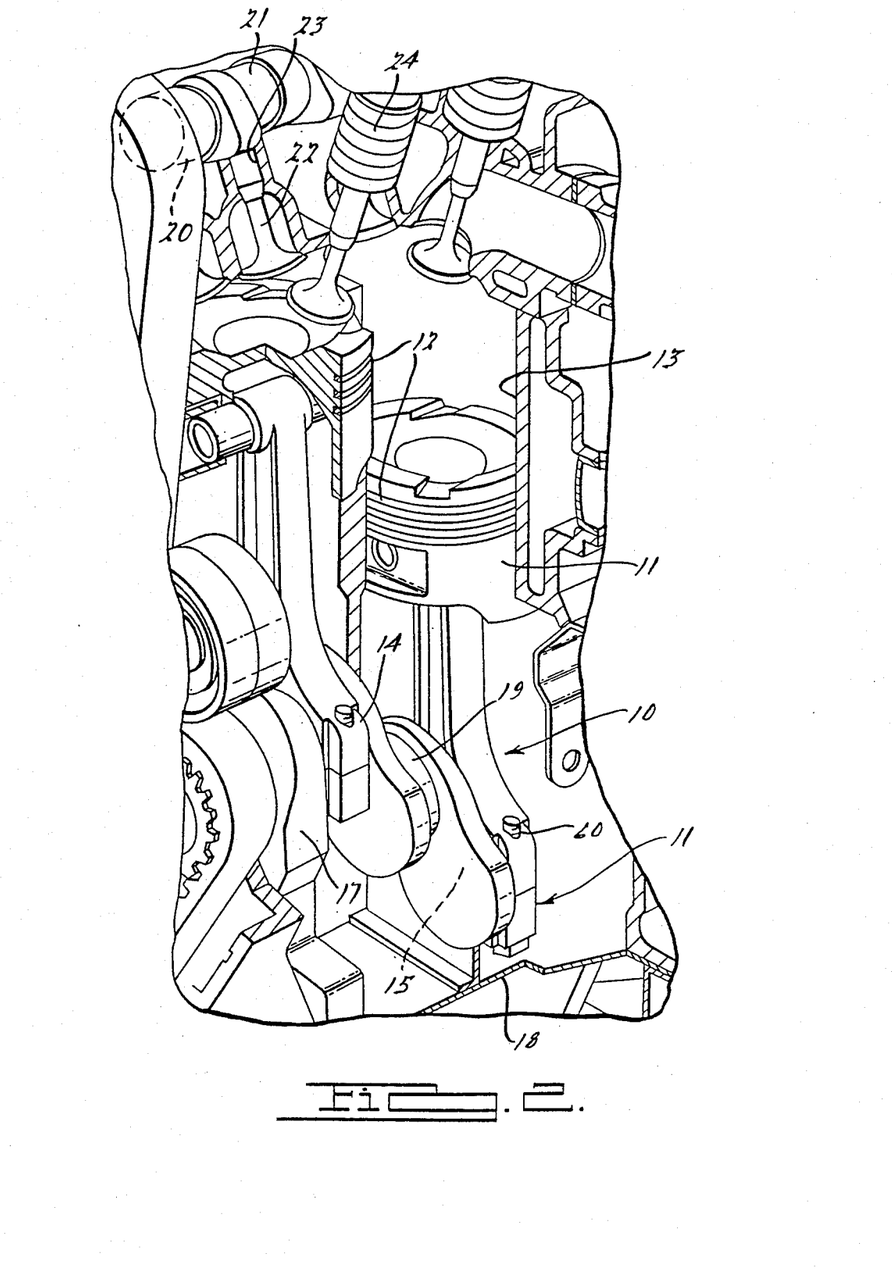
FIG. 2 is a perspective view of a cut-away engine assembly to illustrate location of sliding or rolling contact areas.

A preferred method mode is set forth in the expanded flow diagram of FIG. 1A. The engine subassembly consists of a cylinder block and crankcase with associated moving parts installed therein, such as pistons with piston rings, connecting rods and rod bearings, crankshaft and main bearings. It is possible to test the entire engine as fully assembled, as shown in FIG. 2, but certain areas of concern will be masked and interrupt a clear line of sight to the thermal sensor unless complex mirrors are used. As shown in FIG. 2, areas of concern for the cylinder block and crankcase subassembly 10 are (i) the fit between the piston 11 and piston rings 12 to the cylinder bore 13 which represent first sliding contact surfaces, (ii) the rolling contact fit between the bearing sleeves in the big end 14 of the connecting rod and the crank arm 15 of the crankshaft 16, and (iii) the rolling contact fit between the main bearings at each bulkhead of the crankcase 18 and the main shaft 19 of the crankshaft 16. In a head assembly, the areas of concern are (i) the rolling contact fit between bearings 20 for the camshaft 21 and the camshaft itself, (ii) the sliding fit between the valve stem 22 and the valve guides 23, and (iii) the action of the valve springs 24.

SIMULATED OPERATION

Figure 3:
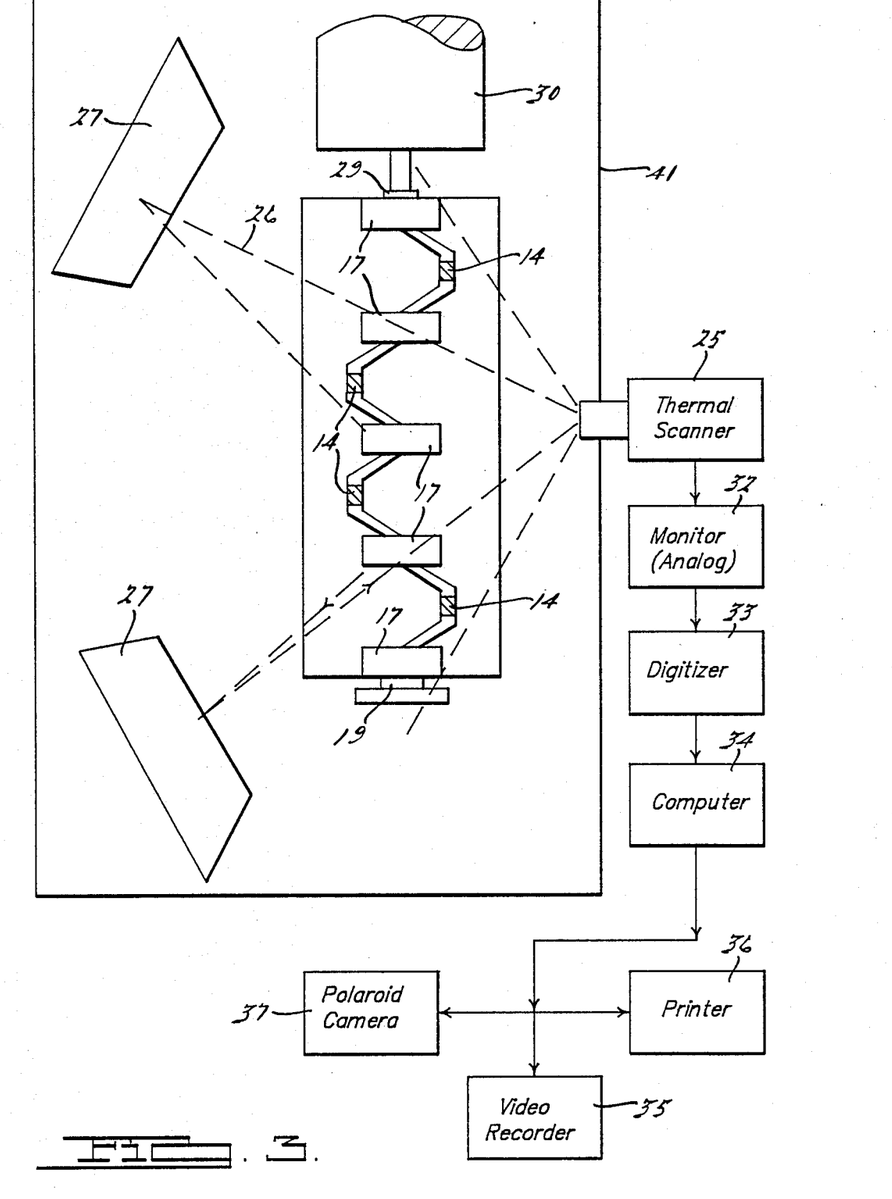
FIG. 3 is a schematic diagram of an apparatus layout used to carry out the method of this invention.

The output shaft 29 of the crankshaft 19 of subassembly 10 is connected to an electric drive motor 30, as shown in FIG. 3. The movable parts of the subassembly are motored or driven without firing (combustion in the cylinder bore) and at ambient temperature conditions. The cylinder block-crankcase subassembly is shown with its bottom up, having the main bearings 17 for the crankshaft on top, and the bearings for the connecting rod big end 14 exposed therebetween. The fit between the piston and cylinder bore is underneath, but can be viewed from a side elevation viewpoint. The crankshaft is turned at a speed of about 750 rpm.

Figure 4:
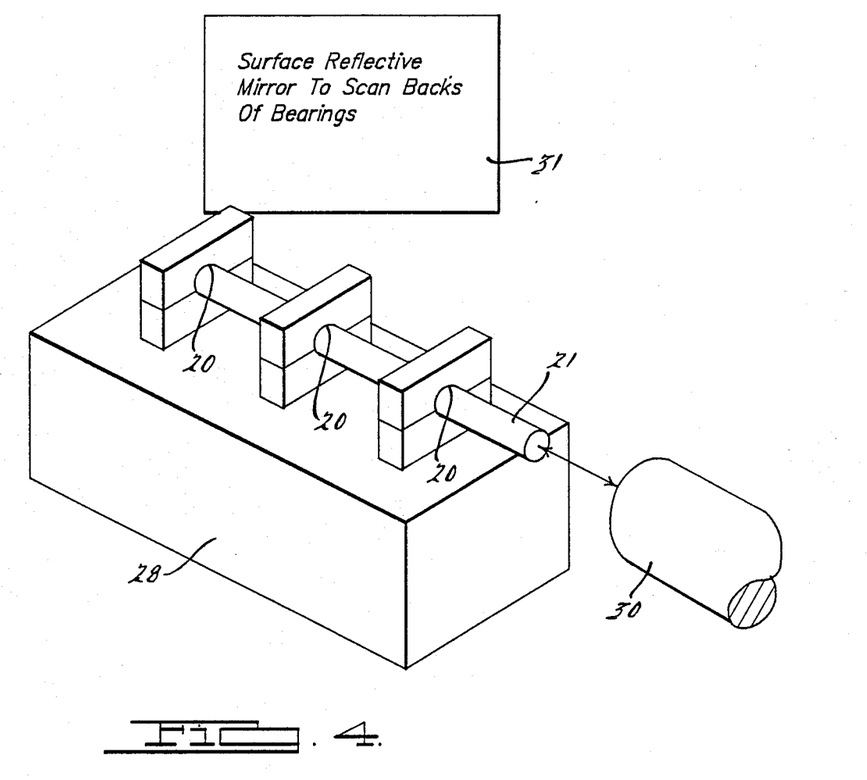
FIG. 4 is an alternative engine head subassembly viewed from an angled perspective.
Figure 8:
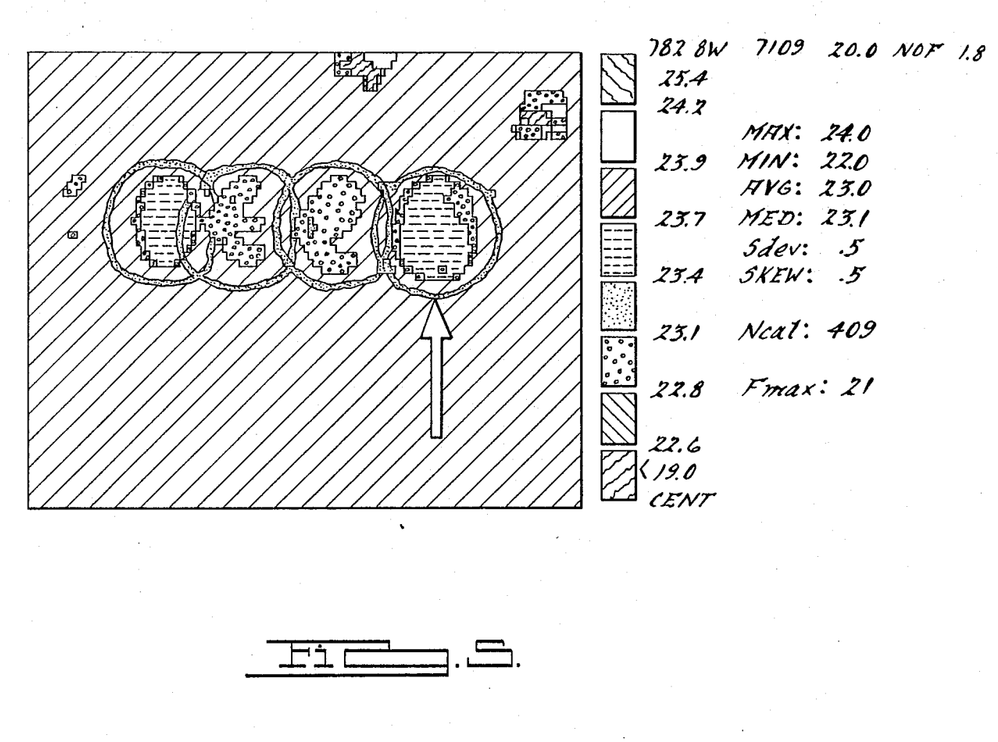

As shown schematically in FIG. 4, the subassembly of only the engine head 28 and its associated moving parts may be subjected to simulated operation. The input member (camshaft 21) is connected to an electric drive motor for operation at intended speeds for such member. The front of the camshaft bearings 20 can be viewed from a perspective as illustrated in FIG. 4 and the rear of the bearings 20 can be viewed by use of one or more mirrors 31.

Out of dimension defects can occur in the cylinder block-crankcase subassembly by the fit of the piston being undersized, oversized, or the piston rings folded out of position either in or out of the piston grooves or missing piston rings. A condition of oversize can occur by installation of a piston into a cylinder bore that reduces the piston to bore clearance beyond the minimum permitted. For example, in a typical 1.9L engine, the acceptable range of piston to bore clearance is 0.0012–0.0020 inches (clearance is the total diametrical difference). If such clearance is reduced below the minimum by an oversized piston, the thermal camera will detect such. With a thermal camera having a resolution power of 0.5 C°, an oversize defect of as little as 0.0005 inch can be detected in 10 seconds when compared to a nondefect reference. Similarly, if the maximum clearance is exceeded by an undersized piston for the bore, sufficient thermal emission differences can be detected in 10 seconds of motoring at 0.5 C° resolution power to locate the defect and type it as undersize. Piston oversize or undersize can occur as a result of machining control or dimensional damage after machining or grading. In the assembly of piston to cylinder bores, it is conventional to grade the pistons and cylinders into A through F categories, each differing by 0.0004 inches; accordingly, different grades of pistons are matched with different cylinder bores to meet the clearance tolerance range, such as 0.0012–0.0020 inches. This invention locates and types dimensional aberrations that exceed such range even after such matching is carefully conducted during assembly.

In automotive main bearings for the crankshaft, it is typical to design in a clearance tolerance of 0.0008–0.0026 inches (0.020–0.065 mm) and similarly for connecting rod bearings, it is typical to design in the same clearance. Deviations beyond this range of as little as 0.001 inch can easily be detected by a thermal sensor with a resolution power of 0.5 C° during a motoring time span of 10 seconds or less.

SENSING AND THERMAL MAPPING

As shown in FIG. 3, a thermal camera 25 is directed at the automotive engine subassembly to sense infrared radiation during a time span of 2–10 seconds measured from the initiation of the simulated operation. The camera may be positioned generally in the same horizontal plane that passes through the bearings for the crankshaft and preferably is directed slightly downwardly at an angle of about 30° with respect to such plane to have a line-of-sight to the entire annular character of the piston rings. The camera or sensing mechanism may be selected from one of the following: a thermal camera, a radiometer, and a thermal line scanner. Preferably, an infrared thermal camera is employed for carrying out the preferred mode herein, such camera having a field of view which encompasses both ends of the subassembly and a depth of field which can encompass the front and back of the subassembly.

The sensing mechanism can have a resolution power that can distinguish changes in infrared radiation corresponding to 0.02-1.0 C°, but sensitivity within the range of 0.1-0.7 C° is best because it does not generate false signals. A thermal camera with resolution power of 0.1-0.7 C° will be able to distinguish a spectrum of at least eight colors for color prints or at least eight gradations of gray for computer imaging.

To more effectively sense infrared radiation, a plurality of thermal cameras may be employed which, of course, adds to the expense of the apparatus; this may be reduced by employing mirrors 27 to substitute for the additional cameras, permitting viewing of the back side of bearings along a line of sight 26 as shown in FIG. 3.

The output from the thermal camera or imaging will be voltage signals corresponding to the location in the scan of the camera and as a function of time. These signals are received by a monitor 32 and are converted to a digitized signal by digitizer 33. The output of the digitizer is connected to a computer 34 which manipulates the digitized signal. Such computer should have a capacity sufficient to receive rapid signal sensations which may result from the thermal camera being run at a range of 20-35 frames per second. The output of computer 34 can be selectively directed to a video recorder 35 (which provides for a thermal map imaging), a printer 36, or memorialized in polaroid film by an instant-type camera 37.

To more effectively eliminate any interference, such as from fluorescent lighting that may be in the test room, the engine is placed in a black box 41.

The sensed digitized signals are compared to reference digitized signals for the same subassembly that is known to have no defects. Thermal mapping comparison will thus allow the tester to determine where a defect exists and what type of defect, i.e., whether oversize or undersize. The reference digitized signals must be adjusted to compensate for any differing ambient thermal conditions. The computer techniques to implement the method steps of this invention are known to those skilled in the art.

FIG. 5 shows a computer generated thermal map for a cylinder block subassembly with the thermal camera pointed directly down onto the open cylinder bores. Cylinder bore #4 (which is circled) shows a graded image that corresponds to an excess temperature (23.9-24.2 C°) beyond the predetermined permissible temperature range of up to 24.0 C°; this imaging occurred after eight seconds of motoring.

While particular embodiments of the invention have been illustrated and described, it will be obvious to those skilled in the art that various changes and modifications may be made without departing from the invention, and it is intended to cover in the appended claims all such modifications and equivalents as fall within the true spirit and scope of the invention. For example, the thermal camera viewing angle may be varied from that shown in FIGS. 3 and 4. The camera may be placed directly over the top of the cylinder block in an upright position, using mirrors to receive thermal emissions from underneath the block.

We claim:

1. A method of determining the location and type of dimensional defects in an assembly having certain sliding or rolling contact surfaces during simulated operation of such assembly and before any damage results to such assembly, comprising:
    (a) initiating simulated operation of said assembly;
    (b) sensing any change in the temperature of said assembly surrounding the location of each said certain sliding or rolling contact surface (i) with a resolution power of 0.02-1.0 C° and (ii) during a time span of 2-10 seconds measured from such initiation to provide separated voltage signals for each location;
    (c) digitizing said signals; and
    (d) comparing the sensed digitized signals with reference digitized signals for such an assembly without defects operated during the same time span and adjusted to compensate for any differing ambient thermal conditions, any deviations detected by such comparison representing defects.

2. The method as in claim 1, in which in step (b) the sensing is carried out by the use of infrared thermography.

3. The method as in claim 2, in which said simulated operation is at ambient conditions and said thermography is carried out by use of a device selected from the group consisting of: a thermal camera, a radiometer, and a thermal line scanner.

4. The method as in claim 2, in which in step (c) said signal is converted to a digitized thermal map and the comparison in step (d) is carried out with a reference digitized thermal map.

5. The method as in claim 2, in which said resolution power of step (b) is 0.1-0.7 C°.

6. The method as in claim 2, in which said comparing determines plus or minus deviations corresponding to oversize or undersize fit between the certain sliding or rolling contact surfaces.

7. The method as in claim 1, in which said thermal sensing is carried out by use of a single thermal camera and by use of a plurality of mirrors at remote locations about said assembly to sense infrared radiation from hidden locations about the assembly.

8. The method as in claim 1, in which said sensing is carried out by the use of a plurality of thermal cameras.

9. The method as in claim 1, in which said sensing is carried out with the rolling contact surfaces protected by a black chamber to eliminate radiation interference.

10. The method as in claim 1, in which said sensing is effective to discriminate parts out of dimension by at least 0.0005 inches.

11. The method as in claim 1, in which said assembly is an automotive engine, and said sensing has a resolution effective to detect undersized or oversized clearances at crankshaft, connecting rod bearings and pistons.

12. The method as in claim 11, in which the detected clearances between said crankshaft or connecting rod and bearings is 0.001 inch or greater, and the detected clearances between said pistons and cylinder bores is 0.0005 inch or greater.

13. A method of determining the location and type of friction generating defects in an engine subassembly containing pistons, connecting rods and crankshaft, comprising:
    (a) motoring such subassembly at ambient conditions on-line during engine assembly;
    (b) sensing the infrared thermal emission of said subassembly at one or more predetermined focus locations (i) within a resolution power of 0.1-0.7 C° change and (ii) during a time span of 2-10 seconds measured from the initiation of said motoring to provide a continuous analog signal;

(c) converting said signal to a digitized thermal map within a computer;

(d) comparing the sensed digitized thermal map to a reference digitized thermal map (i) for such an engine subassembly known to be without defects, (ii) operated during the same time span, and (iii) adjusted to compensate for any differing ambient conditions;

(e) transport said subassembly off-line if said comparison indicates a deviation in temperature of plus or minus the resolution power of said sensing from the reference digitized thermal map at a zone of said sensed digitized thermal map associated with selected sliding or rolling contact surfaces;

(f) repair defect at zone location indicated in step (e) for said deviation; and (g) return to on-line assembly for repeat of steps (a)–(f).

14. The method as in claim 13, in which deviations are detectable for piston fit that correspond to as little as 0.0005 inch in undersize and 0.0010 inch in oversize.

* * * * *